United States Patent [19]

Laurens et al.

[11] 3,930,730

[45] Jan. 6, 1976

[54] INTERFEROMETRIC DEVICE FOR MEASUREMENT OF VARIATIONS IN LENGTH OF A SAMPLE UNDER THE INFLUENCE OF TEMPERATURE

[75] Inventors: Albert Adelin Suffrein Laurens, Paris; Jean-Paul Christy, Neuilly-sur-Seine; Jean-Pierre Durand, Paris, all of France

[73] Assignee: Republic of France, Paris, France

[22] Filed: Sept. 6, 1973

[21] Appl. No.: 394,552

[30] Foreign Application Priority Data
Sept. 6, 1972 France ............................ 72.31505

[52] U.S. Cl. ............................. 356/106 R; 356/109
[51] Int. Cl.² .......................................... G01B 9/02
[58] Field of Search ........ 356/106 R, 108, 109, 110, 356/112, 113

[56] References Cited
UNITED STATES PATENTS
3,788,746  1/1974  Baldwin .......................... 356/106 R OTHER PUBLICATIONS
Bennett; S. J., "A Double–Passed Michelson Interferometer," *Optics Communications*, Vol. 4, No. 6, p. 428, Feb./Mar. 1972.

Primary Examiner—Ronald L. Wibert
Assistant Examiner—Conrad Clark
Attorney, Agent, or Firm—Larson, Taylor & Hinds

[57] ABSTRACT

An interferometric device is provided for measurement of the variations in length of a sample under the influence of temperature, the length of the sample being within a plane of reference and a plane of measurement defined by two plane terminal faces of the sample. The device comprises a source of monochromatic light, means to form parallel beams from the light source, a controllable temperature thermostatic enclosure containing a sample holder, a reflecting measurement surface joined to the plane of measurement for receiving one of the beams, a reflecting reference surface for receiving the other beam, a bearing face presented by the sample holder for the terminal reference face of the sample which is elastically applied against the bearing face, and support means for supporting the reflecting reference surface inside the enclosure and ensuring that the variation of distance between the two reflecting surfaces will always be equal to the variation in length of the sample when the temperature of the thermostatic enclosure is varied. The two beams reflected respectively by the two reflecting surfaces are caused to interfere, and a sensor observes and measures interference fringes.

8 Claims, 10 Drawing Figures

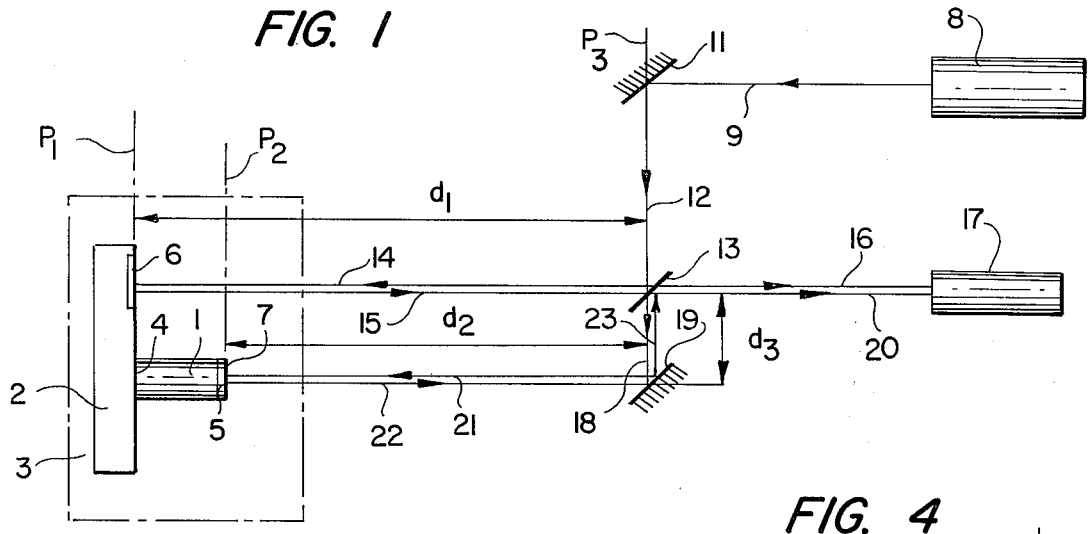
FIG. 1
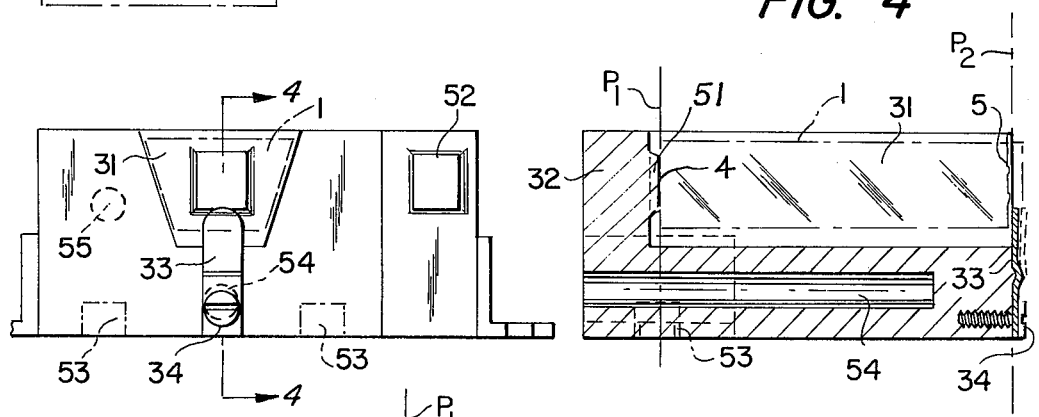
FIG. 4
FIG. 3
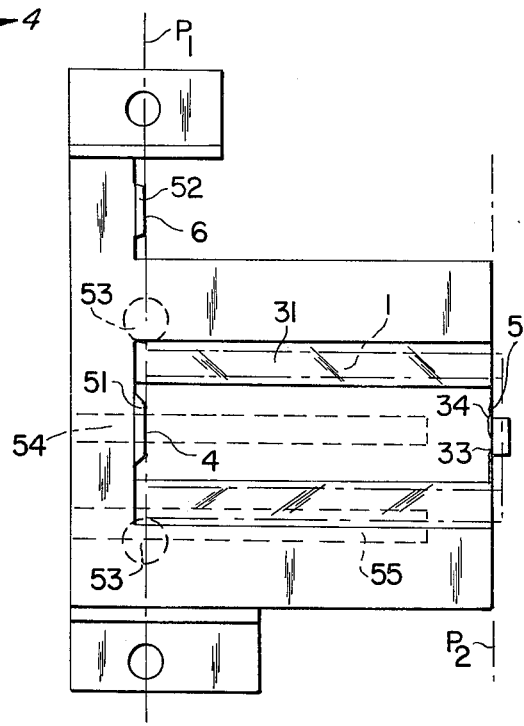
FIG. 5

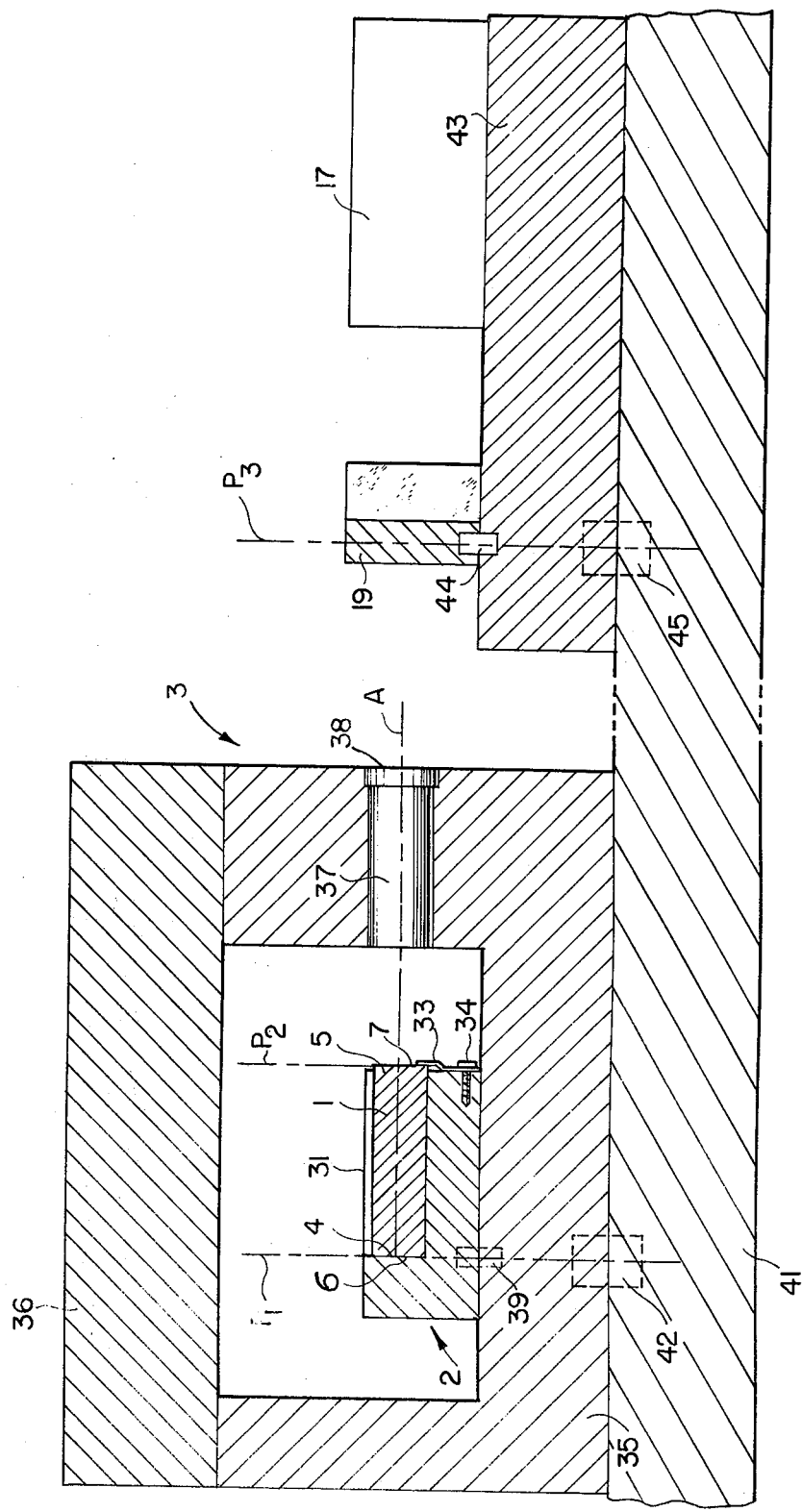

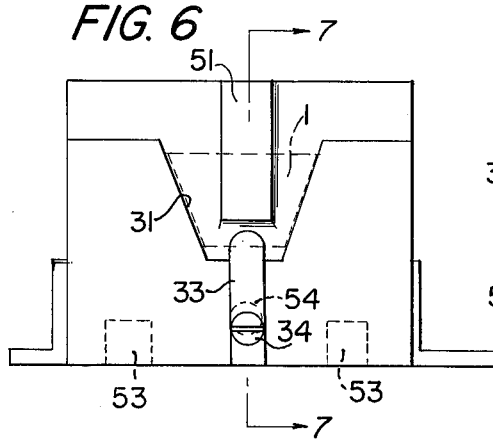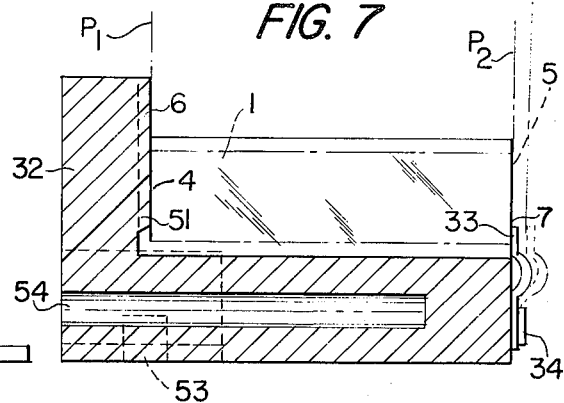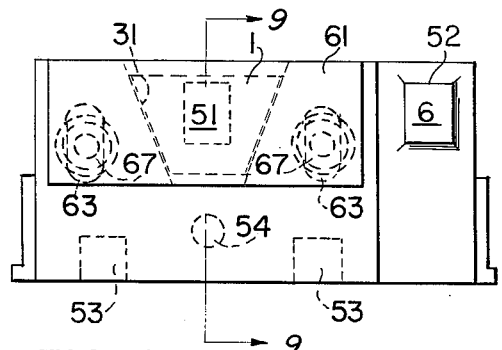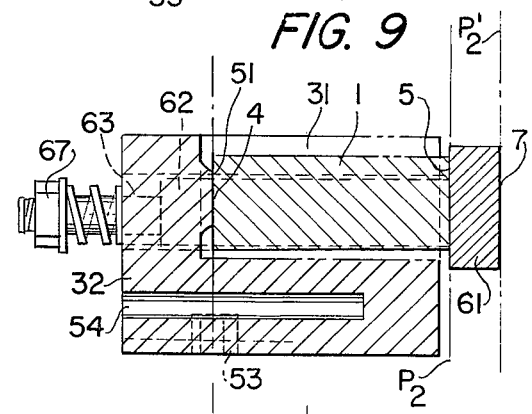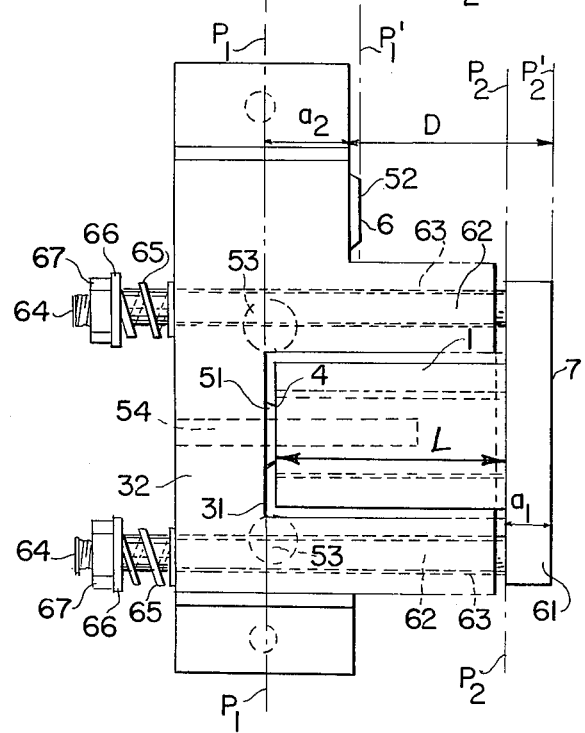

3,930,730

INTERFEROMETRIC DEVICE FOR MEASUREMENT OF VARIATIONS IN LENGTH OF A SAMPLE UNDER THE INFLUENCE OF TEMPERATURE

FIELD OF THE INVENTION

The present invention relates to a device for interferometric measurement of variations in length of a sample, under the influence of temperature.

BACKGROUND AND SUMMARY

Interferometric measuring devices for determination of length are known which are suitable for study of samples that are of sufficient dimensions.

But these known devices are poorly adapted to the measurement of small samples with a low coefficient of dilatation, as in the case when a material is received for the first time, for example material obtained by crystal growth, in very small dimensions. It is important in numerous cases to be able to determine with good precision the coefficient of thermal dilatation of this new material, to decide if it is suitable for the purpose that is sought before engaging large amounts of money to get larger samples.

The invention is intended to remedy these drawbacks, with development of a device that can be rapidly and readily adapted to samples of different sizes, and that assures rapid placement and precise positioning of the sample that is to be measured.

According to the invention, an interferometric device for measurement of variations in length of a sample under the influence of temperature, said length being between a plane of reference and a measurement plane defined by the two plane terminal faces of the sample, comprising a source of monochromatic light, means to form parallel beams from said source, a thermostatic enclosure, means to vary the temperature in the enclosure, a sample holder disposed in the enclosure, a reference reflecting surface, a measuring reflecting surface connected to the measurement plane, means to cause the two beams reflected respectively by the two reflecting surfaces to interfere, and a sensor to observe and measure interference fringes, is improved in that the reference reflecting surface is disposed inside the thermostatic enclosure, and in that the sample holder presents a bearing surface for the terminal reference face of the sample, elastic means are provided to apply the sample against said bearing surface, and a support is provided for the reference reflecting surface, so designed that the variation of distance between the two reflecting surfaces is constantly equal to the variation in length of the sample when the temperature of the thermostatic enclosure is modified.

Other features of the invention will become evident from the detailed description that is to follow.

DESCRIPTION OF THE DRAWINGS

In the attached drawings which are given as non limitative examples, several embodiments of the device are shown.

FIG. 1 is an optical schema corresponding to the device that is the subject of the invention.

FIG. 2 is a view in vertical section representing the whole of the device of the invention.

FIG. 3 is a view in elevation of a first embodiment of the sample holder which is part of the device of FIG. 2.

FIG. 4 is a view in section along IV—IV of FIG. 3.

FIG. 5 is a view in plan of the sample holder of FIG. 3.

FIG. 6 is a view in elevation of a second embodiment of the sample holder that is part of the device of FIG. 2.

FIG. 7 is a view in section along VII—VII of FIG. 6.

FIG. 8 is an elevation of a third embodiment of the sample holder of the invention, which is part of the device of FIG. 2.

FIG. 9 is a view in section along IX—IX of FIG. 8.

FIG. 10 is a plan view of the sample holder of FIG. 8.

According to the optical schema shown in FIG. 1, a sample 1 is placed on a sample holder 2 in a thermostatic enclosure 3, indicated in dot and dash lines. Said enclosure 3 comprises means for adjustment of its temperature and for production of a vacuum, in order to avoid the effect of possible turbulance of the air. Sample 1 presents, at one end, a reference face 4 in a plane of reference $P_1$, bearing on sample holder 2 and, at the other end, a measurement face 5, defining a plane of measurement $P_2$ parallel to plane $P_1$. A reflecting reference surface 6 is rigidly connected to sample holder 2. In the case of the schema, it is in reference plane $P_1$. A measurement reflecting surface 7 is connected to the measurement face 5. Said reflecting surface may, as shown farther on, coincide in plane $P_2$ with measurement face 5. It will be seen subsequently that reflecting surfaces 6 and 7 can be outside planes $P_1$ and $P_2$.

A source 8 of monochromatic light having a certain coherence which may be, but not necessarily so, a laser, is furnished with an optical system whereby it is possible to obtain a parallel beam 9. Said beam is deflected by a mirror 11 inclined at 45° along a beam 12 toward a semitransparent orientable blade 13. Said blade reflects a part of beam 12 and deflects this part orthogonally toward reference surface 6, along a beam 14, itself reflected by surface 6 along a beam 15 that passes through blade 13. Beam 16 issuing from this passage penetrates into a sensor 17. Another part of incident beam 12 passes through blade 13 along a beam 18, then is deflected orthogonally by a mirror 19 that is orientable and movable, toward measurement surface 7 along a beam 21. Said beam is reflected by surface 7 along a beam 22, itself reflected by mirror 19 along a beam 23 that blade 13 reflects along a beam 20 of the same path as beam 16.

To take into account a possible difference between the coefficients of reflection of surfaces 6 and 7, there can be intercalated an optical density, which is not illustrated, on the path of one of the said beams.

A sensor 17 makes it possible visually to observe and to record interferences between beams 16 and 20.

The arrangement is such that the difference in length between the optical paths of the beams reflected respectively by reference surface 6 and measurement surface 7 is sufficiently small so that the interferences can be observed even with a source 8 that is not very coherent, such as a standard source of monochromatic light. In other words $d_1$ is substantially equal to the sum of $d_2$ and $d_3$ (FIG. 1), these symbols designating optical paths. For this, mirror 19 may be moved parallel to the direction of incident beam 12, in correspondence with the various sample holders 2 that are used.

The device just described is controlled as follows, enclosure 3 being at ambient temperature:

the orientation of semitransparent blade 13 is adjusted so that the incident beam 14 and reflected beam 15 coincide.

the orientation of mirror 19 is adjusted so that incident beam 21 and reflected beam 22 coincide.

the setting of mirror 19 is improved by observation of the interference figure in sensor 17. Adjustment is finished when there are no longer localized fringes on reflecting surfaces 6 and 7. In this case there are interference rings to infinity.

If it is preferred to work with a system of fringes, it suffices to touch up the adjustment of mirror 19 to cause appearance of fringes at the desired separation.

When the temperature is raised in enclosure 3, the dilatation of sample 1 causes a difference in length between the optical paths of beams 14 and 15 on the one hand and 18, 21, 22, and 23 on the other. It will be shown that the dispositions that are provided by the invention ensure that the variation of the distance between the two reflecting surfaces 6 and 7 is constantly equal to the variation in length of the sample. In these conditions, the variation of the difference between the optical paths is equal to double the variation of length of the sample which can thus be measured by counting the interference fringes.

It will be noted that fixed mirror 11 is not indispensible. This mirror serves solely to make the device more compact.

The assembly of the device according to the optical schema of FIG. 1 is shown in FIG. 2.

Sample 1 is placed in a seat 31 of sample holder 2, its reference face 4 being applied against a flat part of the base of said seat by a spring 33 fixed by a screw 34.

Enclosure 3 comprises a body 35, a cover 36 and a window 37 for passage of luminous beams. Said window is obturated by a transparent blade 38 which, to avoid parasitic reflections, has its faces slightly inclined with reference to the direction of the light beams that pass through window 37.

Sample holder 2 is positioned in enclosure 3 by two centering feet 39 whose axes are in reference plane $P_1$. The device comprises also a base 41, of material with a low coefficient of thermal dilatation. Body 35 of enclosure 3 is positioned on base 41 by centering feet 42 whose axes are in plane $P_1$ and which are rigidly connected to centering feet 39.

On base 41 there rests a support 43 which bears the optical part of the device, namely source 8, mirrors 11 and 19, blade 13 and sensor 17. The mirrors are positioned with reference to support 43 by centering feet 44 and support 43 itself is positioned with reference to base 41 by centering feet 45, the axes of feet 44 and 45 being in a plane $P_3$ parallel to planes $P_1$ and $P_2$.

The assembly just described offers the following advantages:

Thermostatic enclosure 3 can dilate freely with reference to base 41 and similarly dilatation of sample holder 2 is possible with reference to the thermostatic enclosure. In this way:

The separation between planes $P_1$ and $P_3$ is not influenced by changes of temperature of enclosure 3. If the ambient temperature remains stable during the measurement, base 41 undergoes no dilatation and the distance between planes $P_1$ and $P_3$ remains the same.

Planes $P_1$ and $P_3$ in any case remain parallel and their possible slight variation in separation does not affect the difference between the optical paths of the beams reflected respectively by reference surface 6 and measurement surface 7.

Positioning by centering feet furthermore allows rapid change of sample holder to correspond to the samples to be measured.

A first embodiment of sample holder 2 will now be described, shown in FIGS. 3 to 5, suitable for the case in which the reflecting measurement surface 7 coincides with measurement face 5 in plane $P_2$.

The sample holder comprises a sample seat 31 with straight trapezoidal section, closed at the back by a bottom 32. This presents an elevation 51 whose plane surface serves as a stop for reference face 4 of sample 1, said surface defining reference plane $P_1$. On one side, sample holder 2 presents, on the other hand, a second elevation 52 with plane surface 6 in plane $P_1$, preferably at the same level with reference to the base of the sample holder as the surface of elevation 51. Sample 1 thus also has a trapezoidal section.

Surface 6 is made reflecting by polishing or by coating with a thin film constituting the reflecting reference surface. Measurement face 5 of sample 1 is similarly made reflecting and in this case constitutes the reflecting measurement surface 7 defined above.

At its base, the sample holder presents two recesses 53 to receive centering feet 39 of enclosure 3: the axes of recesses 53 are in plane $P_1$. The sample holder also presents two seats 54 and 55 opening on the rear face and intended to receive thermocouples for measurement of the temperature in the vicinity of sample 1.

It is to be seen that this device allows determination of the variation of the length of sample 1 with rigorous precision, even if the sample is of small dimensions and if its coefficient of thermal dilatation is low.

Because of the trapezoidal configuration of seat 31 and of sample 1, the sample is rigorously positioned with reference to the sample holder no matter what the temperature may be in enclosure 3 and even if the coefficients of dilatation of sample and sample holder are different.

Duration of manipulations is reduced to the minimum. Sample 1 is mounted directly on sample holder 2 and this is placed very rapdily in the enclosure 3 because of centering feet 39. Removal of sample holder 2 from enclosure 3 is also very easy. If a series of experiments has to be run on different samples 1, they can be mounted ahead of time on a series of sample holders 2 which are then placed in enclosure 3 in succession.

A second embodiment of sample holder 2 is shown in FIGS. 6 and 7, constituting a variant of the first embodiment. It differs from the first in that the plane surface of elevation 51 extends above seat 31 of the sample, and is made reflecting in its upper part to constitute the reference reflecting surface 6.

A third embodiment of sample holder 2, represented in FIGS. 8 and 10, is referred particularly to the case in which measurement face 5 of sample 1 cannot be made reflecting by polishing or by application of an adequate thin film.

As in the first embodiment, the sample holder presents, on its bottom 32, an elevation 51 that presents a plane terminal surface determining reference plane $P_1$, against which reference 4 of sample 1 abuts.

Reflecting measurement surface 7 is on the forward face of a support 61 of thickness $a_1$ at ambient temperature and with coefficient $\lambda_1$ of thermal dilatation. Said support is applied against measurement face 5 of sample 1 by straps 62 engaged in hollows 63 that pass through the sample holder. Each strap 62 presents at its rear end a threaded part 64 on which a nut 67 is threaded. A spring 65 bears on the one hand on the bottom of the sample holder and on the other hand on a washer 66 held by nut 67.

Surface 7 determines a plane $P_2'$ parallel to plane of measurement $P_2$, the separation between the two said planes being equal to $a_1$ at ambient temperature.

The sample holder has an elevation 52 whose plane face 6 constitutes the reflecting reference surface in a plane $P_1'$ parallel to reference plane $P_1$ and shifted with reference thereto by a distance $a_2$ at ambient temperature. In the illustrated embodiment, elevation 52 is placed on the side of the sample holder, but it may of course be disposed above the seat of the sample as in the embodiment described above.

By designating the coefficient of thermal dilatation $\lambda_2$ of the material constituting the sample holder, the invention provides that magnitudes $a_1$, $a_2$, $\lambda_1$, $\lambda_2$ will satisfy the equation:

$$a_1\lambda_1 = a_2\lambda_2 \qquad (1)$$

It will readily be seen that distance $D$ between planes $P_1'$ and $P_2'$ that contain the reflecting reference and measurement surfaces is joined to length $L$ of the sample by the equation:

$$D = L + a_1 - a_2 \qquad (2)$$

Equation (1) shows that the variations with the temperature of $a_1$ and $a_2$ are equal. Consequently according to equation (2), variations as a function of the temperature of $D$ and $L$ are also equal to each other.

In the case in which support 61 is made of the same material as the sample holder, we have of course $a_1 = a_2$ and $D = L$.

Of course the invention is not limited to the described embodiments, and there may be numerous variations of execution without exceeding the scope of the invention.

We claim:

1. In an interferometric device for measurement of the variations in length of a sample under the influence of temperature, the length of the sample being within a plane of reference and a plane of measurement defined by two plane terminal faces of the sample, the device comprising a source of monochromatic light, means to form parallel beams from said source, a controllable temperature thermostatic enclosure, a sample holder placed in the enclosure, a reflecting reference surface for receiving one of said beams, a reflecting measurement surface joined to the plane of measurement for receiving the other of said beams, means to cause interferences of the two beams reflected respectively by the two reflecting surfaces, and a sensor to observe and measure interference fringes, the improvement comprising a bearing face presented by said sample holder for the terminal reference face of the sample, elastic means for applying the sample against said bearing face, and support means for supporting said reflecting reference surface inside said enclosure and ensuring that the variation of distance between the two reflecting surfaces will be equal to the variation in length of the sample when the temperature of the thermostatic enclosure is varied, said sample holder comprising a support for the reflecting measurement surface, of thickness $a_1$ and with coefficient of thermal dilatation $\lambda_1$, applied against the terminal measurement face of the sample, the support means for the reflecting reference surface having a thickness $a_2$, measured from the plane of reference, and a coefficient of dilatation $\lambda_2$, and these thicknesses and these coefficients of dilatation satisfying the equation $a_1\lambda_1$ equals $a_2\lambda_2$.

2. Device as in claim 1, wherein the support means for the reflecting reference surface is an integral part of the sample holder.

3. Device as in claim 1 wherein the support of the reflecting measurement surface presents straps that bear elastically against the rear part of the sample holder to apply the support of the reflecting measurement surface against the measurement face of the sample.

4. In an interferometric device for measurement of the variations in length of a sample under the influence of temperature, the length of the sample being within a plane of reference and a plane of measurement defined by two plane terminal faces of the sample, the device comprising a source of monochromatic light, means to form parallel beams from said source, a controllable temperature thermostatic enclosure, a sample holder placed in the enclosure, a reflecting reference surface for receiving one of said beams, a reflecting measurement surface joined to the plane of measurement for receiving the other of said beams, means to cause interferences of the two beams reflected respectively by the two reflecting surfaces, and a sensor to observe and measure interference fringes, the improvement comprising a bearing face presented by said sample holder for the terminal reference face of the sample, elastic means for applying the sample against said bearing face, said sample holder presenting a straight concave seat for the sample of substantially trapezoidal section as viewed parallel to said other of said beams such that said sample lies within the concave seat and is supported by the diverging walls of the trapezoidal section to facilitate maintenance of alignment of the axis of the sample and prevent pinching, swinging or compression of the sample, and support means for supporting said reflecting reference surface inside said enclosure and ensuring that the variation of distance between the two reflecting surfaces will be equal to the variation in length of the sample when the temperature of the thermostatic enclosure is varied.

5. Device as in claim 4, wherein the reflecting measurement surface coincides with the measurement plane of the sample, the reflecting reference surface is in the plane of reference, and said support means is an integral part of the sample holder.

6. In an interferometric device for measurement of the variations in length of a sample under the influence of temperature, the length of the sample being within a plane of reference and a plane of measurement defined by two plane terminal faces of the sample, the device comprising a source of monochromatic light, means to form parallel beams from said source, a controllable temperature thermostatic enclosure, a sample holder placed in the enclosure, a reflecting reference surface for receiving one of said beams, a reflecting measurement surface joined to the plane of measurement for receiving the other of said beams, means to cause interferences of the two beams reflected respectively by the two reflecting surfaces, and a sensor to observe and measure interference fringes, the improvement comprising a bearing face presented by said sample holder for the terminal reference face of the sample, elastic means for applying the sample against said bearing face, support means for supporting said reflecting reference surface inside said enclosure and ensuring that the variation of distance between the two reflecting surfaces will be equal to the variation in length of the sample when the temperature of the thermostatic enclosure is varied, at least two centering feet and corresponding mating formations carried by respective ones of said sample holder and said enclosure for releasably positioning the sample holder in the enclosure, the axes of said centering feet and said mating formations lying substantially in said plane of reference.

7. Device as in claim 6 further comprising a base bearing the enclosure and the means to cause interference of the beams, and at least two centering feet and cooperating mating formations carried by respective ones of said enclosure and said base for positioning the enclosure on the base, the axes of these second-mentioned centering feet and mating formations lying substantially in said plane of reference.

8. Device as in claim 7 further comprising at least two further centering feet, whose axes are in a plane parallel to the plane of reference, for cooperation with mating formations to position on the base supports for said means to cause interference of the beams.

* * * * *